United States Patent
Gupta et al.

(10) Patent No.: US 6,506,765 B2
(45) Date of Patent: Jan. 14, 2003

(54) APOMORPHINE DERIVATIVES AND METHODS FOR THEIR USE

(75) Inventors: Pramod K. Gupta, Gurnee, IL (US); Deborah Milkowski, Chicago, IL (US); Debra Sutkowski-Markmann, Willow Springs, IL (US)

(73) Assignee: TAP Pharmaceutical Products, Inc., Lake Forest, IL (US)

( * ) Notice: Subject to any disclaimer, the term of this patent is extended or adjusted under 35 U.S.C. 154(b) by 0 days.

(21) Appl. No.: 09/821,236

(22) Filed: Mar. 29, 2001

(65) Prior Publication Data

US 2002/0002176 A1 Jan. 3, 2002

Related U.S. Application Data

(60) Provisional application No. 60/195,650, filed on Apr. 7, 2000.

(51) Int. Cl.[7] .............................................. A61K 31/44
(52) U.S. Cl. ......................... 514/284; 514/34; 514/80; 546/77; 546/78
(58) Field of Search ........................ 514/284; 546/77.28

(56) References Cited

U.S. PATENT DOCUMENTS

| | | | |
|---|---|---|---|
| 4,127,118 A | 11/1978 | Latorre | |
| 4,521,421 A | * 6/1985 | Foreman | 514/267 |
| 4,801,587 A | 1/1989 | Voss et al. | |
| 5,256,652 A | 10/1993 | El-Rashidy et al. | |
| 5,624,677 A | 4/1997 | El-Rashidy et al. | |
| 5,756,483 A | 5/1998 | Kerkus | |
| 5,770,606 A | 6/1998 | El-Rashidy et al. | |
| 5,866,164 A | 2/1999 | Kuczynski et al. | |
| 5,888,534 A | 3/1999 | El-Rashidy et al. | |
| 5,925,629 A | * 7/1999 | Place | 514/179 |
| 5,939,094 A | 8/1999 | Durif et al. | |
| 5,945,117 A | 8/1999 | El-Rashidy et al. | |
| 5,985,889 A | 11/1999 | El-Rashidy et al. | |
| 5,994,363 A | 11/1999 | El-Rashidy et al. | |

FOREIGN PATENT DOCUMENTS

| WO | WO 98/31368 | 7/1998 |
|---|---|---|
| WO | WO 99/279905 | 6/1999 |

* cited by examiner

*Primary Examiner*—James H. Reamer
(74) *Attorney, Agent, or Firm*—Wood, Phillips, Katz, Clark & Mortimer

(57) ABSTRACT

Apomorphine derivative compounds; pharmaceutically active compositions of apomorphine derivative compounds; and the use of apomorphine derivative compounds in methods for treating sexual dysfunction or for enhancing apomorphine effectiveness for patients treated with apomorphine are disclosed. The apomorphine derivatives may be esters, ethers, amides, mixed anhydrides, hemiacetals, glucuronates, sulfates or phosphonates. A preferred apomorphine derivative is norapomorphine.

15 Claims, No Drawings

APOMORPHINE DERIVATIVES AND METHODS FOR THEIR USE

CROSS REFERENCE TO RELATED APPLICATIONS

This application claims the benefit of U.S. Provisional Application No. 60/195,650, filed Apr. 7, 2000.

FIELD OF THE INVENTION

The present invention is directed to apomorphine derivative compounds; pharmaceutically active compositions of apomorphine derivative compounds; and the use of apomorphine derivative compounds in methods for treating sexual dysfunction or for enhancing apomorphine effectiveness for patients treated with apomorphine. The apomorphine derivatives may be esters, ethers, amides, mixed anhydrides, hemiacetals, glucuronates, sulfates or phosphonates. A preferred apomorphine derivative is norapomorphine.

BACKGROUND OF THE INVENTION

The human sexual response in both males and females results from a complex interplay of psychological, hormonal and other physiological influences. Efforts are ongoing to provide effective treatments which are convenient and simple to use, do not require a constant dosage regimen or even multiple doses to achieve desired results, are non-invasive and allow a rapid and predictable capacity for sexual function on demand and in response to normal sexual stimulation.

For males, methods involving various external devices for the treatment of impotence have been suggested such as tourniquets (see U.S. Pat. No. 2,818,855). In addition, penile implants, such as hinged or solid rods and inflatable, spring driven or hydraulic models, have been used for some time.

Drug treatments are also known. For example, U.S. Pat. No. 4,127,118 discloses a method of treating male impotence by local injection of an appropriate vasodilator, in particular, an adrenergic blocking agent or a smooth muscle relaxant to effect and enhance an erection, and U.S. Pat. No. 4,801,587 discloses the application of an ointment to relieve impotence. The ointment consists of the vasodilators papaverine, hydralazine, sodium nitroprusside, phenoxybenzamine, or phentolamine and a carrier to assist absorption of the primary agent through the skin. U.S. Pat. No. 5,256,652 discloses the use of an aqueous topical composition of a vasodilator such as papaverine together with hydroxypropyl-β-cyclodextrin.

The effect of apomorphine on impotence, or male sexual dysfunction has been extensively studied and reported upon. However, apomorphine has been shown to have very poor oral bioavailability. See, for example, Baldessarini et al., in Gessa et al., eds., *Apomorphine and Other Dopaminomimetics, Basic Pharmacology*, Vol. 1, Raven Press, N.Y. (1981), pp. 219–228.

Therefore, the efficacy of the use of apomorphine for treatment of sexual dysfunction is reduced by the problems of low bioavailability and undesirable side effects. An increased bioavailability leads to an increase in plasma concentration of the drug and an increase in undesirable side effects. Therefore, for the treatment of sexual dysfunction, use of apomorphine has to date been qualified by specific concentration parameters and/or methods of administration to overcome this problem.

For example, apomorphine has been disclosed for the amelioration of female sexual dysfunction in U.S. Pat. No. 5,945,117. Apomorphine has also been disclosed for the amelioration of male erectile dysfunction in U.S. Pat. Nos. 5,624,677; 5,888,534; 5,770,606; 5,985,889 and 5,994,363. In U.S. Pat. No. 5,624,677, mint flavoring may be added to the formulation to attenuate some of the local emesis receptors. In U.S. Pat. No. 5,888,534, a slow release sublingual tablet is disclosed. The slow release of the tablet is said to reduce the undesirable side effects of the drug. The adverse effects of apomorphine were minimized by gradual acclimatization to apomorphine as disclosed in U.S. Pat. No. 5,994,363. Apomorphine was disclosed for treatment of impotence in a fast release oral formulation when the patient was first pre-treated with domperidone in WO 98/31368. The treatment of erectile dysfunction with certain nasal formulations of apomorphine is disclosed in WO 99/27905. However there is still a need for effective treatments of sexual dysfunction.

It is therefore an object of this invention to provide an effective treatment for sexual dysfunction.

It is a further object of this invention to provide a method for enhancing use of apomorphine, when apomorphine is used to treat patients with Parkinson's disease or sexual dysfunction, among other maladies.

SUMMARY OF THE INVENTION

The present invention is directed to a compound of the structure

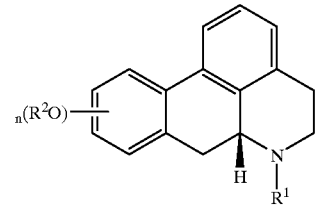

Formula I wherein n is an integer of from one to four;

R$^1$ is selected from the group consisting of hydrogen, alkyl, —PO$_3$H$_2$, —SO$_3$H, and glucuronyl; and, R$^2$ at each occurrence is independently selected from the group consisting of hydrogen, alkyl, —PO$_3$H$_2$, —SO$_3$H and glucuronyl;

or a pharmaceutically acceptable salt thereof.

Preferably, the compound is of the structure

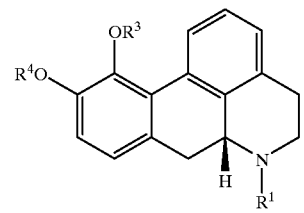

Formula II wherein R$^1$ is selected from the group consisting of hydrogen, alkyl, —PO$_3$H$_2$, —SO$_3$H and glucuronyl; and R$^3$ and R$^4$ are each independently selected from the group consisting of hydrogen, alkyl, —PO$_3$H$_2$, —SO$_3$H and glucuronyl;

or a pharmaceutically acceptable salt thereof.

The invention is also directed to pharmaceutical compositions comprising a compound of Formula I in a pharmaceutically acceptable carrier.

The invention is also directed to a method of treating sexual dysfunction in a patient in need of such treatment comprising administering a therapeutically effective amount of at least one compound of Formula I to said patient. The compound may be an apomorphine derivative which is an ester, ether, amide, mixed anhydride, hemiacetal, glucuronate, sulfate or phosphonate. In the method, apomorphine or a pharmaceutically acceptable salt thereof may also be administered to said patient. A presently preferred compound is norapomorphine.

The invention is also directed to a method for enhancing apomorphine effectiveness in a patient treated with apomorphine comprising the step of co-administering a therapeutically effective amount of a combination of at least one compound of Formula I with apomorphine to said patient. The compound may be an apomorphine derivative which is an ester, ether, amide, mixed anhydride, hemiacetal, glucuronate, sulfate or phosphonate. In the method, apomorphine or a pharmaceutically acceptable salt thereof may also be administered to said patient. A presently preferred compound is norapomorphine.

Presently preferred apomorphine derivatives include apomorphine N-glucuronide, apomorphine O-glucuronide, apomorphine O-sulfate, apomorphine N-sulfate, norapomorphine, norapomorphine O-glucuronide, norapomorphine N-glucuronide, norapomorphine O-sulfate, norapomorphine N-sulfate and combinations thereof. For the practice of the method, the patients may be those treated for Parkinson's disease or sexual dysfunction.

When the method is used for the treatment of sexual dysfunction and the patient is male, the therapeutically effective amount may be an amount sufficient to induce an erection adequate for vaginal penetration. Alternatively, if the patient is female the therapeutically effective amount may be an amount sufficient to induce clitoral erectogenesis and vaginal engorgement. In the methods, apomorphine may administered intranasally, orally, sublingually or administered by inhalation to the lungs.

DETAILED DESCRIPTION OF THE INVENTION

Definitions of Terms

The term "alkyl" as used herein alone or in combination refers to $C_1$–$C_{12}$ straight or branched, substituted or unsubstituted saturated chain radicals derived from saturated hydrocarbons by the removal of one hydrogen atom, unless the term alkyl is preceded by a $C_x$–$C_y$ designation. Representative examples of alkyl groups include methyl, ethyl, n-propyl, iso-propyl, n-butyl, sec-butyl, iso-butyl, and tert-butyl among others.

The term "glucuronyl" as used herein refers to a group of the general structure —C(O)(CH(OH))$_4$—CO$_2$H. Glucuronyl derivatives (or glucuronides) are obtained by reacting glucuronic acid through the aldehyde moiety with the compound to be derivatized. Alcohol or amine functionalities on a compound may be glucuronidated.

Use of the above terms is meant to encompass substituted and unsubstituted moieties. Substitution may be by one or more electron-donating or electron withdrawing groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

As used herein, the term "composition" is intended to encompass a product comprising the specified ingredients in the specified amounts, as well as any product which results, directly or indirectly, from a combination of the specified ingredients in the specified amounts.

The terms "co-administered" or "co-treated" used herein indicates treatment with two or more pharmacological agents together in a single unit dosage form or alternatively, in two or more separate unit dosage forms, one immediately following the other.

Sexual Dysfunction

In males, the form of sexual dysfunction is erectile dysfunction. A normal erection occurs as a result of a coordinated vascular event in the penis. This is usually triggered neurally and consists of vasodilation and smooth muscle relaxation in the penis and its supplying arterial vessels. Arterial inflow causes enlargement of the substance of the corpora cavernosa. Venous outflow is trapped by this enlargement, permitting sustained high blood pressures in the penis sufficient to cause rigidity. Muscles in the perineum also assist in creating and maintaining penile rigidity. Erection may be induced centrally in the nervous system by sexual thoughts or fantasy, and is usually reinforced locally by reflex mechanisms. Erectile mechanics are substantially similar in the female for the clitoris.

Impotence or male erectile dysfunction is defined as the inability to achieve and sustain an erection sufficient for intercourse. Impotence in any given case can result from psychological disturbances (psychogenic), from physiological abnormalities in general (organic), from neurological disturbances (neurogenic), hormonal deficiencies (endocrine) or from a combination of the foregoing. Impotence may be hormonal, congenital, vascular or partial ability, among others.

These descriptions are not exact, however. There is currently no standardized method of diagnosis or treatment. As used herein, psychogenic impotence is defined as functional impotence with no apparent overwhelming organic basis. It may be characterized by an inability to have an erection in response to some stimuli (e.g., masturbation, spontaneous nocturnal, spontaneous early morning, video erotica, etc.) but not others (e.g., partner or spousal attention).

Females also can have sexual dysfunction that increases with age and is associated with the presence of vascular risk factors and onset of menopause. Some of the vascular and muscular mechanisms that contribute to penile erection in the male are believed to be similar vasculogenic factors in female genital response. It is known that in women, sexual arousal is accompanied by arterial inflow which engorges the vagina and increases vaginal lubrication and that the muscles in the perineum assist in achieving clitoral erection.

In the female, sexual dysfunction can arise from organic and psychogenic causes or from a combination of the foregoing. Female sexual dysfunction includes a failure to attain or maintain vaginal lubrication-swelling responses of sexual excitement until completion of the sexual activity. Organic female sexual dysfunction is known to be related in part to vasculogenic impairment resulting in inadequate blood flow, vaginal engorgement insufficiency and clitoral erection insufficiency.

Moreover, sexual dysfunction also includes disorders of orgasm, response timing, ejaculation, nociception, congestive arousal or desire.

The Apomorphine Derivatives

When a patient is administered apomorphine, metabolites are generated in vivo such as esters, ethers, amides, mixed anhydrides, hemiacetals, glucuronates, sulfates and phosphonates. This group of compounds is characterized by its ability to influence dopaminergic, serotonergic, oxytocinergic and nitroxidergic pathways centrally or peripherally to improve conditions such as sexual dysfunction. Some specific examples include morapomorphine, which is N-demethylated apomorphine or O- or N-substituted compounds such as sulfate or glucuronide derivatives of apomorphine and norapomorphine, among others. Such derivatives are also available synthetically. If produced in vivo as a result of treatment with apomorphine, these derivatives may be secreted in bile and may be hydrolyzed in the intestinal lumen, and thereafter circulate enterohepatically. Alternatively, the patient may be treated with the derivatives directly.

The derivatives may be delivered for treatment through acute action, daily administration, or as a chronic agent.

These norapomorphine or apomorphine derivatives can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al describe pharmaceutically acceptable salts in detail in *J. Pharmaceutical Sciences*, 1977, 66:1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salts. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

The derivatives according to the invention can be administered as a nasal spray, nasal drop, suspension, gel, ointment, cream or powder. The administration of the nasal composition may also take place using a nasal tampon or nasal sponge.

Powders can be administered using a nasal insufflator. Powders can also be used in such a manner that they are placed in a capsule. The capsule is set in an inhalation or insufflation device. A needle is penetrated through the capsule to make pores at the top and the bottom of the capsule, and air is sent to blow out the powder particles. Powder formulations can also be administered in a jet-spray of an inert gas or suspended in liquid organic fluids.

The derivatives may be included in a pharmaceutical composition comprising an apomorphine derivative and a physiologically tolerable diluent. The present invention includes apomorphine derivatives and salts thereof as described above formulated into compositions together with one or more non-toxic physiologically tolerable or acceptable diluents, carriers, adjuvants or vehicles that are collectively referred to herein as diluents for intranasal delivery or for oral administration in solid or liquid form.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars and sodium chloride, among others.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others.

Useful intranasal formulations contain a stabilizer and a surfactant. Among the pharmaceutically acceptable surfactants are polyoxyethylene castor oil derivatives, such as polyoxyethylene-glycerol-triricinoleate, also known as polyoxyl 35 castor oil (CREMOPHOR EL), or poloxyl 40 hydrogenated castor oil (CREMOPHOR RH40) both available from BASF Corp.; mono-fatty acid esters of polyoxyethylene (20) sorbitan, such as polyoxyethylene (20) sorbitan monolaurate (TWEEN 80), polyoxyethylene monostearate (TWEEN 60), polyoxyethylene (20) sorbitan monopalmitate (TWEEN 40), or polyoxyethylene 20 sorbitan monolaurate (TWEEN 20) all available from ICI Surfactants of Wilmington, Del.); polyglyceryl esters, such as polyglyceryl oleate; and polyoxyethylated kernel oil (LABRAFIL, available from Gattefosse Corp.) Preferably, the surfactant will be between about 0.01% and 10% by weight of the pharmaceutical composition.

Among the pharmaceutically useful stabilizers are antioxidants such as sodium sulfite, sodium metabisulfite, sodium thiosulfate, sodium formaldehyde sulfoxylate, sulfur dioxide, ascorbic acid, isoascorbic acid, thioglycerol, thioglycolic acid, cysteine hydrochloride, acetyl cysteine, ascorbyl palmitate, hydroquinone, propyl gallate, nordihydroguaiaretic acid, butylated hydroxytoluene, butylated hydroxyanisole, alpha-tocopherol and lecithin. Preferably, the stabilizer will be between about 0.01% and 5% by weight of the pharmaceutical composition.

Chelating agents such as ethylene diamine tetraacetic acid, its derivatives and salts thereof, dihydroxyethyl glycine, citric acid and tartaric acid among others may also be utilized.

Proper fluidity can be maintained, for example, by the use of coating materials such as lecithin, by the maintenance of the required particle size in the case of dispersions and by the use of surfactants.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

The derivatives may also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Compounds for Co-Administration with the Apomorphine Derivatives

The apomorphine derivatives of the present invention may be co-administered with apomorphine, as the apomorphine derivatives may enhance the activity of apomorphine. Apomorphine ((R)-5,6,6a,7-tetrahydro-6-methyl-4H-dibenzo-[de,g]quinoline-10,11-diol) can be represented by the formula

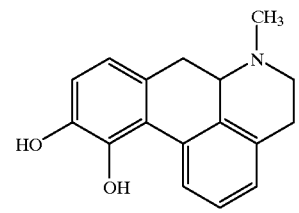

and exists in a free base form or as an acid addition salt. For the purposes of the present invention, apomorphine hydrochloride is preferred, however other pharmacologically acceptable salts thereof can be utilized as well.

Apomorphine has been disclosed as useful in intranasal formulations for the treatment of Parkinson's disease in U.S. Pat. No. 5,756,483. Apomorphine transdermal administration has been disclosed in U.S. Pat. No. 5,939,094; and apomorphine in capsule form has been disclosed in U.S. Pat. No. 5,866,164.

Apomorphine is a dopamine receptor agonist that has a recognized use as an emetic when administered subcutaneously in about a 5 milligram dose. For the purposes of the present invention, apomorphine is administered in an amount sufficient to excite cells in the mid-brain region of the patient but with minimal side effects. This cell excitation is believed to be part of a cascade of stimulation that is likely to include neurotransmission with serotonin, dopamine and oxytocin.

The dopamine receptors in the mid-brain region of a patient can be stimulated to a degree sufficient to cause an erectile response without inducing nausea by the administration, preferably sublingually, of apomorphine, the apomorphine derivatives, or a combination of apomorphine and at least one apomorphine derivative so as to maintain a plasma concentration of apomorphine of no more than about 5.5 nanograms per milliliter (5.5 ng/ml). The sublingual administration usually takes place over a period of time in the range of about 2 to about 10 minutes, or longer. The amount of apomorphine, the apomorphine derivatives, or a combination of apomorphine and at least one apomorphine derivative administered sublingually over this time period preferably is in the range of about 25 micrograms per kilogram ($\mu$g/kg) of body weight to about 60 $\mu$g/kg of body weight.

In sensitive patients experiencing nausea, the onset of nausea can be obviated or delayed by delivering apomorphine, the apomorphine derivatives, or a combination of apomorphine and at least one apomorphine derivative at a controlled dissolution rate so as to provide circulating serum levels and midbrain tissue levels of apomorphine less than 5.5 nanograms/mL. When apomorphine, the apomorphine derivatives, or a combination of apomorphine and at least one apomorphine derivative are administered at or near the higher amounts of the aformentioned dosage range, the likelihood of the onset of nausea can be reduced by concurrent administration of a ganglionic agent (inhibitor of ganglionic response and anti-emetic agent) such as nicotine or lobeline sulfate. For this purpose, the weight ratio of apomorphine, the apomorphine derivatives, or a combination of apomorphine and at least one apomorphine derivative to ganglionic agent is in the range of about 10 to 1.

Other anti-emetic agents that can be used in conjunction with apomorphine, the apomorphine derivatives, or a combination of apomorphine and at least one apomorphine derivative are anti-dopaminergic agents such as metoclopramide, and the phenothiazines, e.g., chlorpromazine, prochlorperazine, pipamazine, thiethylperazine and oxypendyl hydrochloride among others. Also suitable are the serotonin (5-hydroxytryptamine or 5-HT) antagonists such as domperidone, ondansetron (commercially available as the hydrochloride salt under the designation ZOFRAN) among others, the histamine antagonists such as buclizine hydrochloride, cyclizine hydrochloride, dimenhydrinate (DRAMAMINE) among others, the parasympathetic depressants such as scopolamine, as well as other anti-emetics such as metopimazine, trimethobenzamide, benzauinamine hydrochloride, and diphenidol hydrochloride among others.

The plasma concentration of apomorphine, the apomorphine derivatives, or a combination of apomorphine and at least one apomorphine derivative should be maintained at up to about 10 nanograms per milliliter.

The apomorphine derivatives may be co-administered with centrally acting agents such as melanocyte stimulating hormone analogs or adrenoceptor agonists; with hormones such as androgenic compounds, estrogens or progestins; or peripherally acting agents such as alpha adrenoceptor blockers, phosphodiesterase inhibitors, K$^+$ channel agents or with gene therapy.

The following Example is presented to describe preferred embodiments and utilities of the invention and is not meant to limit the invention unless otherwise stated in the claims appended hereto.

EXAMPLE 1

An apomorphine derivative, norapomorphine was evaluated for binding activity at various receptors of neurotransmitters, possible involved in erectile function.

Routine radioligand binding assays were performed using reference standards according to established methodology. IC$_{50}$ values were determined by a non-linear least square regression analysis. K$_i$ values were calculated using the observed IC$_{50}$ of the test compound, the concentration of the radioligand used in the assay and the K$_d$ of the ligand.

The results are shown in Table 1, and are compared to those for apomorphine. The results are listed in descending order of potency for apomorphine. No significant binding activity was observed with apomorphine at the following receptors: dopamine (D$_{4.2}$, D$_{4.4}$, D$_{4.7}$), serotonin (5-HT$_4$), adrenergic ($\beta_1$, $\beta_2$, $\beta_3$), opiate ($\mu$, $\delta$, $\kappa$), tachykinin (NK$_1$, NK$_2$, NK$_3$), neuropeptide Y (NPY$_1$, NPY$_2$), calcitonin gene related peptide (CGRP), vasoactive intestinal peptide (VIP$_1$), muscarinic (M$_1$, M$_2$, M$_3$, M$_4$, M$_5$), nicotinic and gamma aminobutyric acid (GABA$_A$, GABA$_B$). Norapomorphine did not bind significantly to the above receptors either, with the exception of the opiate receptor as indicated in the Table. In addition, neither apomorphine nor its metabolite norapomorphine demonstrated any significant effect on the activity of nitric oxide synthetase.

TABLE 1

| Receptor | Apomorphine K$_i$ (nM) | Norapomorphine K$_i$ (nM) |
| --- | --- | --- |
| Dopamine D$_3$ | 3 | 117 |
| Adrenergic $\alpha_{2B}$ | 4.1 | 213 |
| Dopamine D$_{2S}$ | 18 | 1100 |
| Adrenergic $\alpha_{2C}$ | 19 | N/S |
| Dopamine D$_{2L}$ | 24 | N/S |
| Serotonin 5-HT$_{2A}$ | 27 | 1120 |
| Serotonin 5-HT$_{1A}$ | 37 | 439 |
| Serotonin 5-HT$_7$ | 65 | 1380 |
| Dopamine D$_5$ | 68 | N/S |
| Adrenergic $\alpha_{2A}$ | 71 | 1430 |
| Serotonin 5-HT$_2$ | 111 | N/S |
| Dopamine D$_1$ | 138 | N/S |
| Serotonin 5-HT$_{5A}$ | 185 | N/S |
| Serotonin 5-HT$_{1B}$ | 205 | 3560 |
| Serotonin 5-HT$_6$ | 206 | 1670 |
| Serotonin 5-HT$_3$ | 237 | N/S |
| Serotonin 5-HT$_{1D}$ | 288 | N/S |
| Adrenergic $\alpha_{1A}$ | 343 | 4170 |
| Adrenergic $\alpha_{1D}$ | 588 | N/S |
| Adrenergic $\alpha_{1B}$ | 882 | N/S |
|  |  | Opiate $\mu$ = 2090 |

N/S = no significant activity ($\geq$50% at 10 $\mu$M)

The present invention is illustrated by way of the foregoing description and Example. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims.

We claim:
1. A compound of the structure

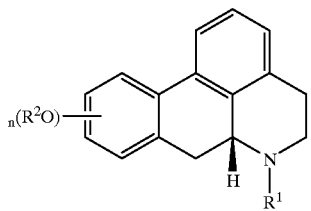

wherein n is an integer of from one to four;
$R^1$ is selected from the group consisting of hydrogen, alkyl, —$PO_3H_2$, —$SO_3H$, and glucuronyl; and,
$R^2$ at each occurrence is independently selected from the group consisting of hydrogen, alkyl, —$PO_3H_2$, —$SO_3H$ and glucuronyl;
or a pharmaceutically acceptable salt thereof provided that $R^1$ cannot be methyl when $R^2$ is hydrogen.
2. The compound of claim 1 of the structure
wherein $R^1$ is selected from the group consisting of hydrogen, alkyl,

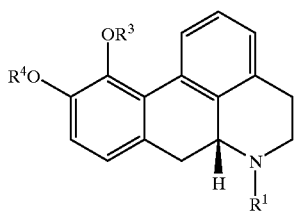

—$PO_3H_2$, —$SO_3H$ and glucuronyl; and
$R^3$ and $R^4$ are each independently selected from the group consisting of hydrogen, alkyl, —$PO_3H_2$, —$SO_3H$ and glucuronyl;
or a pharmaceutically acceptable salt thereof.
3. The compound of claim 1 selected from the group consisting of apomorphine N-glucuronide, apomorphine O-glucuronide, apomorphine O-sulfate, apomorphine N-sulfate, norapomorphine, norapomorphine O-glucuronide, norapomorphine N-glucuronide, norapomorphine O-sulfate and norapomorphine N-sulfate.
4. A pharmaceutical composition comprising:
a compound of claim 1 in a pharmaceutically acceptable carrier.
5. A method of treating sexual dysfunction in a patient in need of such treatment comprising
administering a therapeutically effective amount of at least one compound of claim 1 to said patient.
6. The method of claim 5 wherein said compound is selected from the group consisting of apomorphine N-glucuronide, apomorphine O-glucuronide, apomorphine O-sulfate, apomorphine N-sulfate, norapomorphine, norapomorphine O-glucuronide, norapomorphine N-glucuronide, norapomorphine O-sulfate, norapomorphine N-sulfate and combinations thereof.
7. The method of claim 5 further comprising administering apomorphine or a pharmaceutically acceptable salt thereof to said patient.
8. The method of claim 5 wherein said patient is male and said therapeutically effective amount is an amount sufficient to induce an erection adequate for vaginal penetration.
9. The method of claim 5 wherein said patient is female and said therapeutically effective amount is an amount sufficient to induce clitoral erectogenesis and vaginal engorgement.
10. A method of treating sexual dysfunction in a patient in need of such treatment comprising
administering a therapeutically effective amount of at least one apomorphine derivative selected from the group consisting of esters, ethers, amides, mixed anhydrides, hemiacetals, glucuronates, sulfates and phosphonates to said patient.
11. A method for enhancing apomorphine effectiveness in a patient treated with apomorphine comprising the step of
co-administering a therapeutically effective amount of a combination of at least one compound of claim 1 with apomorphine to said patient.
12. The method of claim 11 wherein said compound is selected from the group consisting of apomorphine N-glucuronide, apomorphine O-glucuronide, apomorphine O-sulfate, apomorphine N-sulfate, norapomorphine, norapomorphine O-glucuronide, norapomorphine N-glucuronide, norapomorphine O-sulfate, norapomorphine N-sulfate and combinations thereof.
13. The method of claim 11 wherein said apomorphine is administered for the treatment of Parkinson's disease or sexual dysfunction.
14. A method for enhancing apomorphine effectiveness in a patient treated with apomorphine comprising the step of
co-administering a therapeutically effective amount of a combination of at least one apomorphine derivative selected from the group consisting of esters, ethers, amides, mixed anhydrides, hemiacetals, glucuronates, sulfates and phosphonates with apomorphine to said patient.
15. A method for enhancing apomorphine effectiveness in a patient treated with apomorphine comprising the step of
co-administering a therapeutically effective amount of a combination of norapomorphine with apomorphine to said patient.

* * * * *